(12) United States Patent
Li et al.

(10) Patent No.: US 11,974,732 B2
(45) Date of Patent: May 7, 2024

(54) SYSTEM AND METHOD FOR URINE ANALYSIS AND PERSONAL HEALTH MONITORING

(71) Applicants: Chun S. Li, Sunnyvale, CA (US); Richard Y. Li, Buffalo, NY (US)

(72) Inventors: Chun S. Li, Sunnyvale, CA (US); Richard Y. Li, Buffalo, NY (US)

(*) Notice: Subject to any disclaimer, the term of this patent is extended or adjusted under 35 U.S.C. 154(b) by 866 days.

(21) Appl. No.: 17/070,598

(22) Filed: Oct. 14, 2020

(65) Prior Publication Data

US 2021/0022646 A1 Jan. 28, 2021

Related U.S. Application Data

(63) Continuation-in-part of application No. 15/694,517, filed on Sep. 1, 2017, now abandoned.

(51) Int. Cl.
*A61B 10/00* (2006.01)
*A61B 5/00* (2006.01)
(Continued)

(52) U.S. Cl.
CPC .......... *A61B 10/007* (2013.01); *A61B 5/1032* (2013.01); *A61B 5/20* (2013.01);
(Continued)

(58) Field of Classification Search
CPC ....... A61B 10/007; A61B 5/1032; A61B 5/20; A61B 5/6898; A61B 5/743; A61B 5/0002; A61B 2010/0006; A61B 2562/0295; A61B 5/14507; A61B 5/1455; G06V 10/56; G06V 10/761; G06V 10/225; G06F 18/22; G06T 7/0012; G06T 7/90; G01N 21/293; G01N 33/493; G01N 2021/7759; G01N 21/78; G01N 33/48792
See application file for complete search history.

(56) References Cited

U.S. PATENT DOCUMENTS

2012/0106811 A1* 5/2012 Chen ...................... B01L 3/5023
422/402
2013/0338464 A1* 12/2013 Stainken ............ A61B 5/15186
600/365
(Continued)

*Primary Examiner* — Dennis White
(74) *Attorney, Agent, or Firm* — Olav M. Underdal; IDP Patent Services

(57) ABSTRACT

A system for urine analysis and personal health monitoring includes a testing box, including a testing chamber, a camera aperture, a visual check aperture, and a test slot, an interchangeable color pattern chart, including a bar code, a base color calibration strip, a test result area, and a test lookup area; a diagnostic analysis server, and a diagnostic analysis device, including a processor, a diagnostic manager, a camera manager, an image analyzer, a camera calibrator, and a camera; such that the diagnostic analysis device captures an original image of the testing chamber interior with a test strip inserted, and analyzes a diagnostic portion of the original image and calculates a test result. Also disclosed is a method for diagnostic analysis, including installing interchangeable color pattern chart, depositing sample, inserting test strip, capturing image, performing color calibration, reading bar code, extracting test strip image, performing color conversion, and calculating test result.

23 Claims, 10 Drawing Sheets

System for Diagnostic Analysis

(51) Int. Cl.
  *A61B 5/103* (2006.01)
  *A61B 5/20* (2006.01)
  *G06V 10/22* (2022.01)
  *G06V 10/56* (2022.01)
  *G06V 10/74* (2022.01)

(52) U.S. Cl.
  CPC ............ *A61B 5/6898* (2013.01); *A61B 5/743* (2013.01); *G06V 10/56* (2022.01); *G06V 10/761* (2022.01); *G06V 10/225* (2022.01)

(56) References Cited

U.S. PATENT DOCUMENTS

| | | | |
|---|---|---|---|
| 2014/0375803 A1* | 12/2014 | Quilter | H04N 7/185 |
| | | | 348/143 |
| 2016/0041152 A1* | 2/2016 | Zimmerle | G01N 21/251 |
| | | | 362/8 |
| 2017/0023542 A1* | 1/2017 | Wang | H04N 5/2257 |
| 2019/0194484 A1* | 6/2019 | Villwock | C09D 11/328 |

* cited by examiner

System for Diagnostic Analysis

System for Diagnostic Analysis

Inside Bottom Plate

Original Image

Inside Top Plate

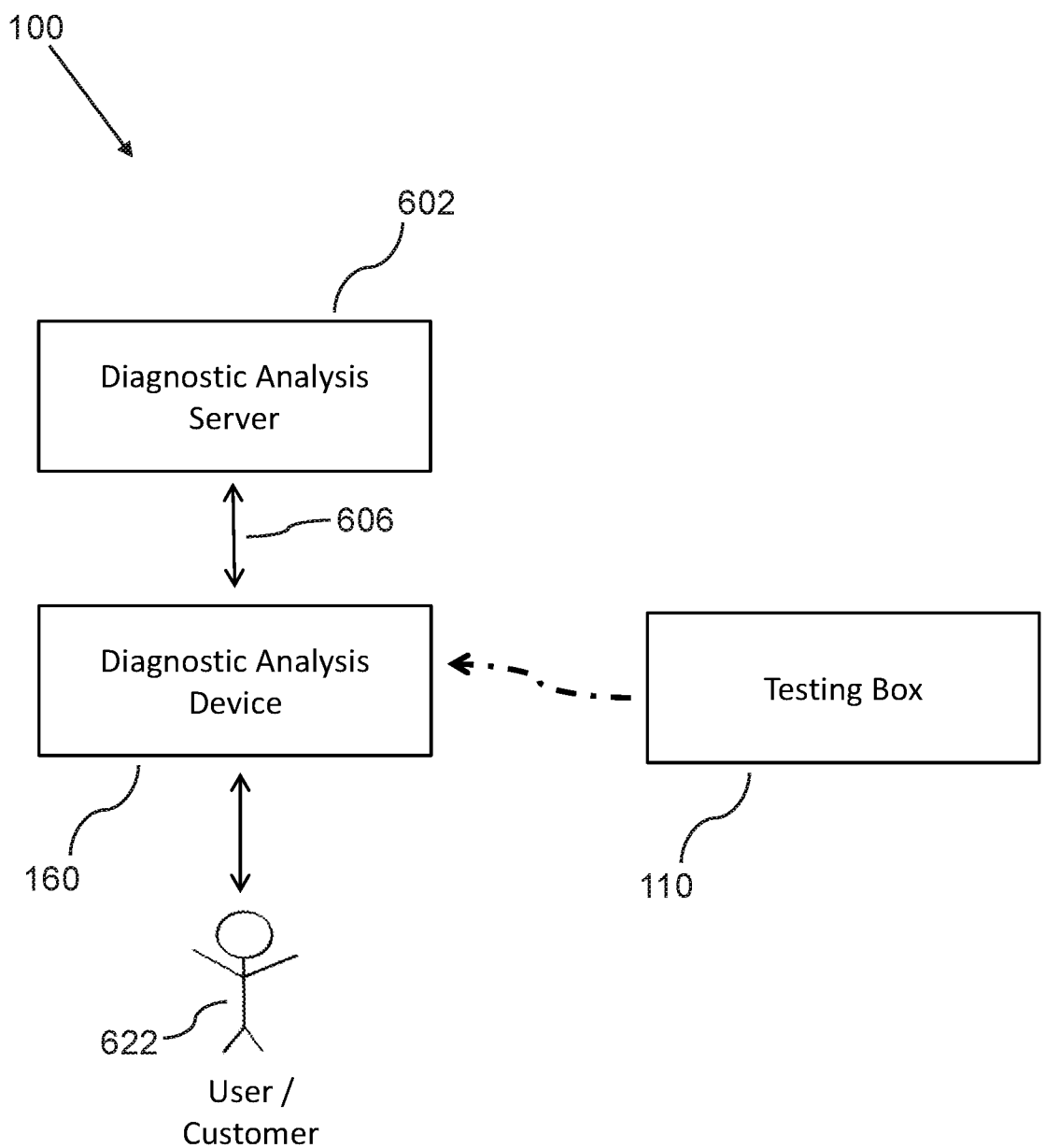

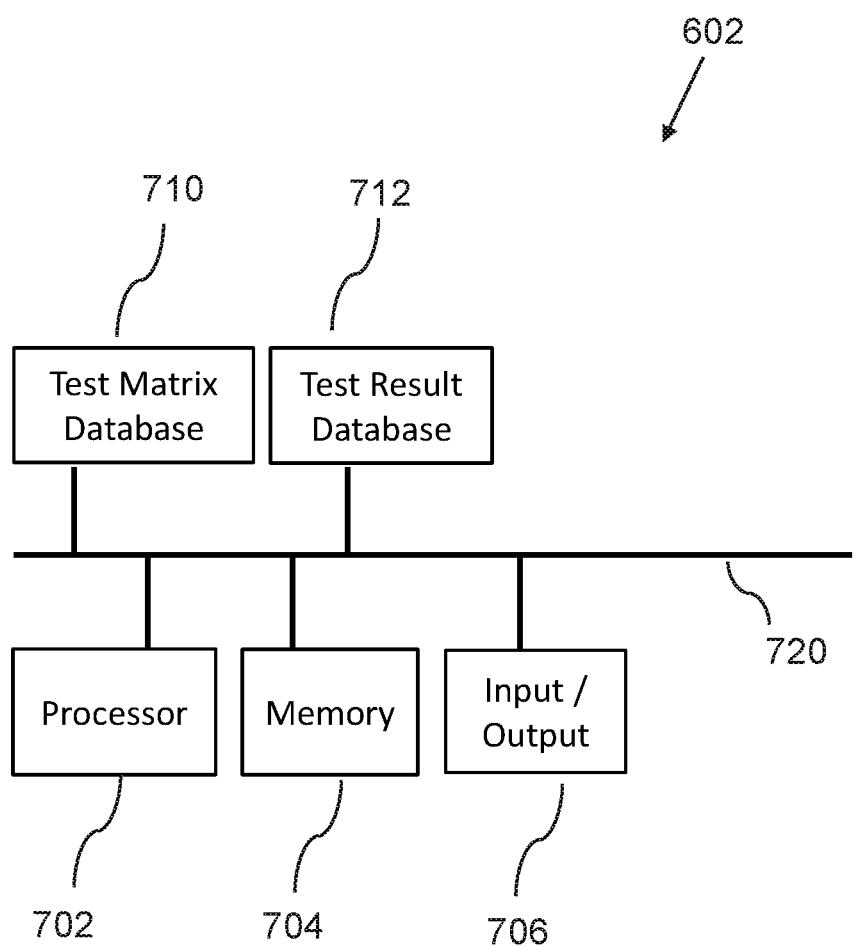

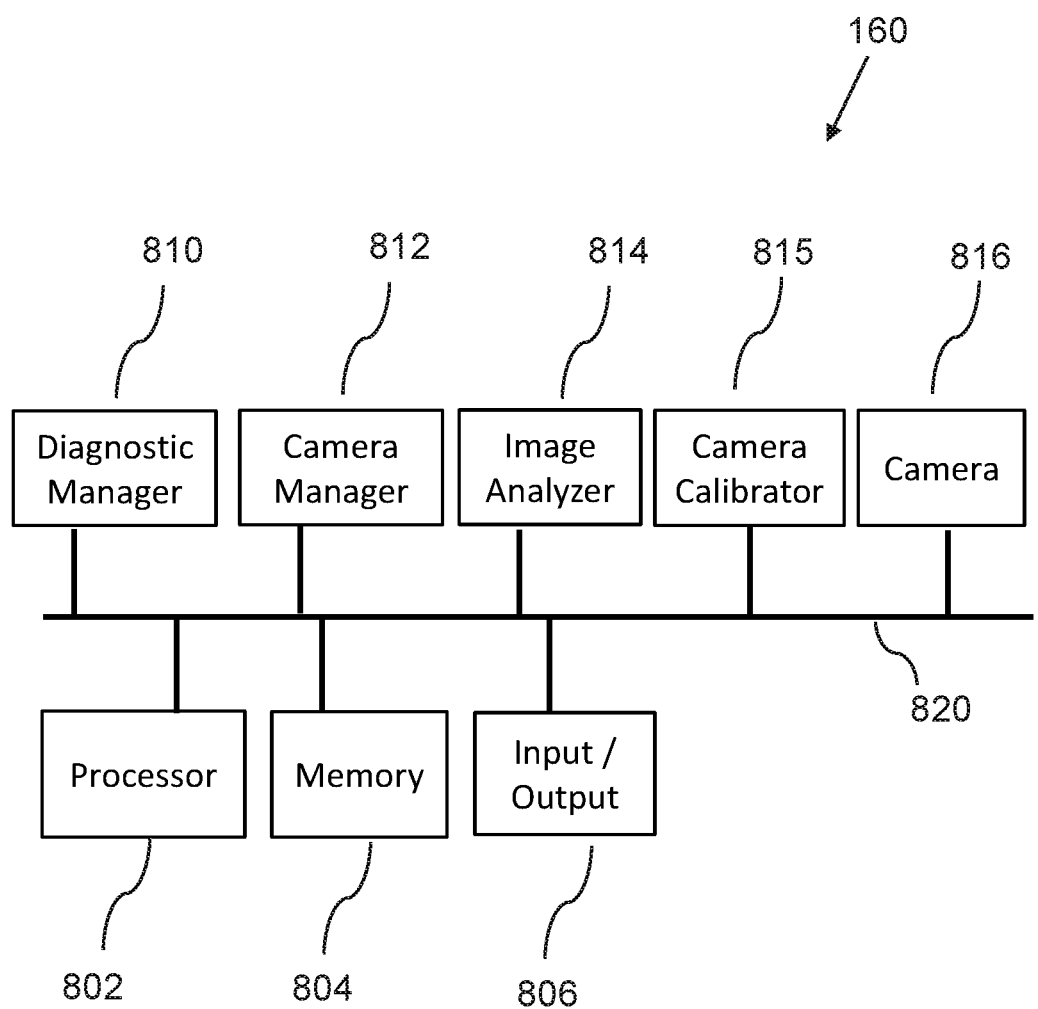

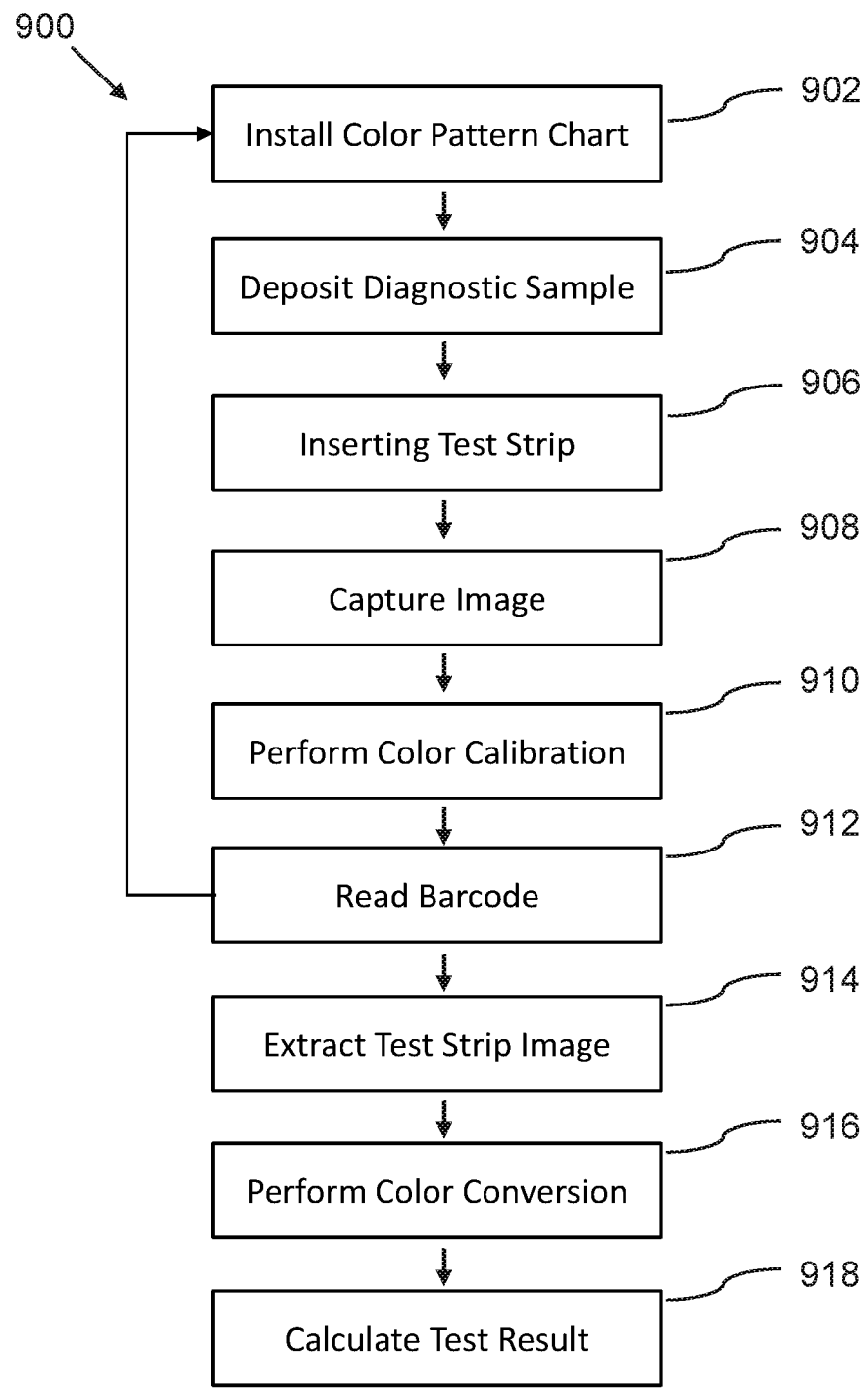

SYSTEM AND METHOD FOR URINE ANALYSIS AND PERSONAL HEALTH MONITORING

CROSS-REFERENCE TO RELATED APPLICATIONS

This U.S. Non-Provisional application is a Continuation-In-Part of U.S. Non-Provisional application Ser. No. 15/694,517, filed Sep. 1, 2017; which is hereby incorporated herein by reference in its entirety.

FIELD OF THE INVENTION

The present invention relates generally to the field of healthcare and point-of-care testing, and more particularly to methods and systems for smartphone-based rapid diagnostic analysis at home, personal health monitoring through non-invasive urine tests, as well as personal health data management and analytics applications.

BACKGROUND OF THE INVENTION

Current medical urine analyzing devices largely use optical reflectance photometry technology, reagent pads illuminated by lighting sources, the reflected light is received by spherical integrators. Photocells are used to measure light wavelengths with filter lens for both testing object and reference beam. Selections of wavelength results are determined by test subjects. The firmware inside analyzers is pre-configured to certain reagent strip in order to properly interpret test results. An analyzer can therefore only work with one type of test strips. The devices used for medical diagnosis in general are quite sophisticated, expensive and bulky. Operations are largely performed by certified professionals.

There has for several years been an increasing consumer demand for fast diagnostic tests at home, for example for testing using urine reagent test strips for manual comparisons with a test chart.

However, such devices are cumbersome in use, and may be inaccurate due to lack of training for proper operations and/or insufficient lightings, etc.

As such, considering the foregoing, it may be appreciated that there continues to be a need for novel and improved devices and methods for diagnostic analysis.

SUMMARY OF THE INVENTION

The foregoing needs are met, to a great extent, by the present invention, wherein in aspects of this invention, enhancements are provided to the existing model of reagent diagnostic analysis.

In an aspect, a system for diagnostic analysis, can include:
a) a testing box, including:
  a testing chamber, which is a cavity inside the testing box;
  a camera aperture, which is an aperture in the testing box, for example a round hole on a top of the testing box, such that the camera aperture provides visual access to the testing chamber;
  a test slot, which is an aperture in the testing box that allows insertion of a test strip into the testing chamber;
  a visual check aperture, which is an aperture that provides visual access to the testing chamber, such that the visual check aperture allows human monitoring and verification; and
b) a diagnostic analysis device (e.g. a smartphone or a mobile device with appropriate app installed) with a camera, such that the diagnostic analysis device is positioned on the testing box with the camera adjacent to the camera aperture, such that when the test strip is inserted into the test slot, the diagnostic analysis device can capture an image of the inside of the testing chamber, the image including a diagnostic image part of a diagnostic portion of the test strip;
  such that the diagnostic analysis device is configured to analyze the diagnostic portion of the image and calculate test results.

In a related aspect, the system for diagnostic analysis can further include:
a) an interchangeable color pattern chart, comprising:
  a bar code, such that the bar code is configured to identify the interchangeable color pattern chart;
  a base color calibration strip, comprising a red calibration area, a green calibration area, and a blue calibration area;
  a test result area, which is configured to receive the test strip when the test strip is inserted through the test slot into the testing chamber; and
  a test lookup area, which includes a plurality of test color strips, each test color strip including a plurality of test results, each test result including a color sample and a numeric test result that is associated with the color sample, such that the test results are ordered by numeric test results.

In another related aspect, an inside top of the testing box can further include:
a) a light-emitting diode assembly, which is configured to illuminate the interchangeable color pattern chart; and
b) the camera aperture.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 6 is a schematic diagram illustrating a system for diagnostic analysis, according to an embodiment of the invention.

FIG. 7 is a schematic diagram illustrating a diagnostic analysis server, according to an embodiment of the invention.

FIG. 8 is a schematic diagram illustrating a diagnostic analysis device, according to an embodiment of the invention.

FIG. 9 is a flowchart illustrating steps that may be followed, in accordance with one embodiment of a method or process of diagnostic analysis.

DETAILED DESCRIPTION

Figure 1A:
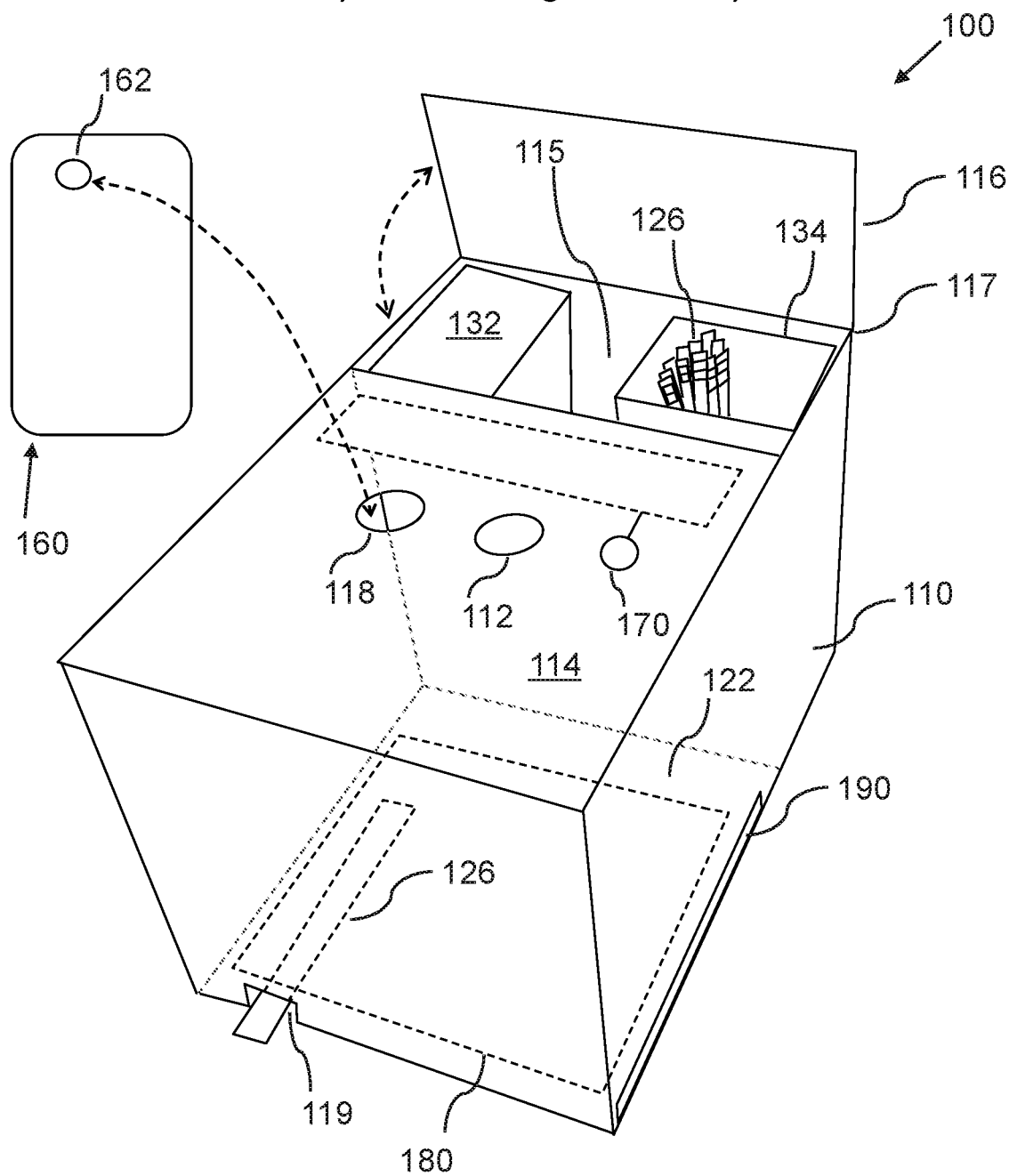
FIG. 1A is a perspective view of a system for diagnostic analysis, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of a system for diagnostic analysis 100 with reference to FIG. 1A, in such manner that like reference numerals refer to like components throughout; a convention that we shall employ for the remainder of this specification.

In various embodiments, the system for diagnostic analysis 100 provides a system and supports methods for users to perform reagent strip type diagnostic tests using smartphones at home or point-of-care. This system is a useful means of monitoring personal health situations with up to 14 health status indicators. The test results are saved and analyzed locally with smartphones, and also with cloud storage and systems for online access, analysis and reporting through the associated app.

Figure 1B:
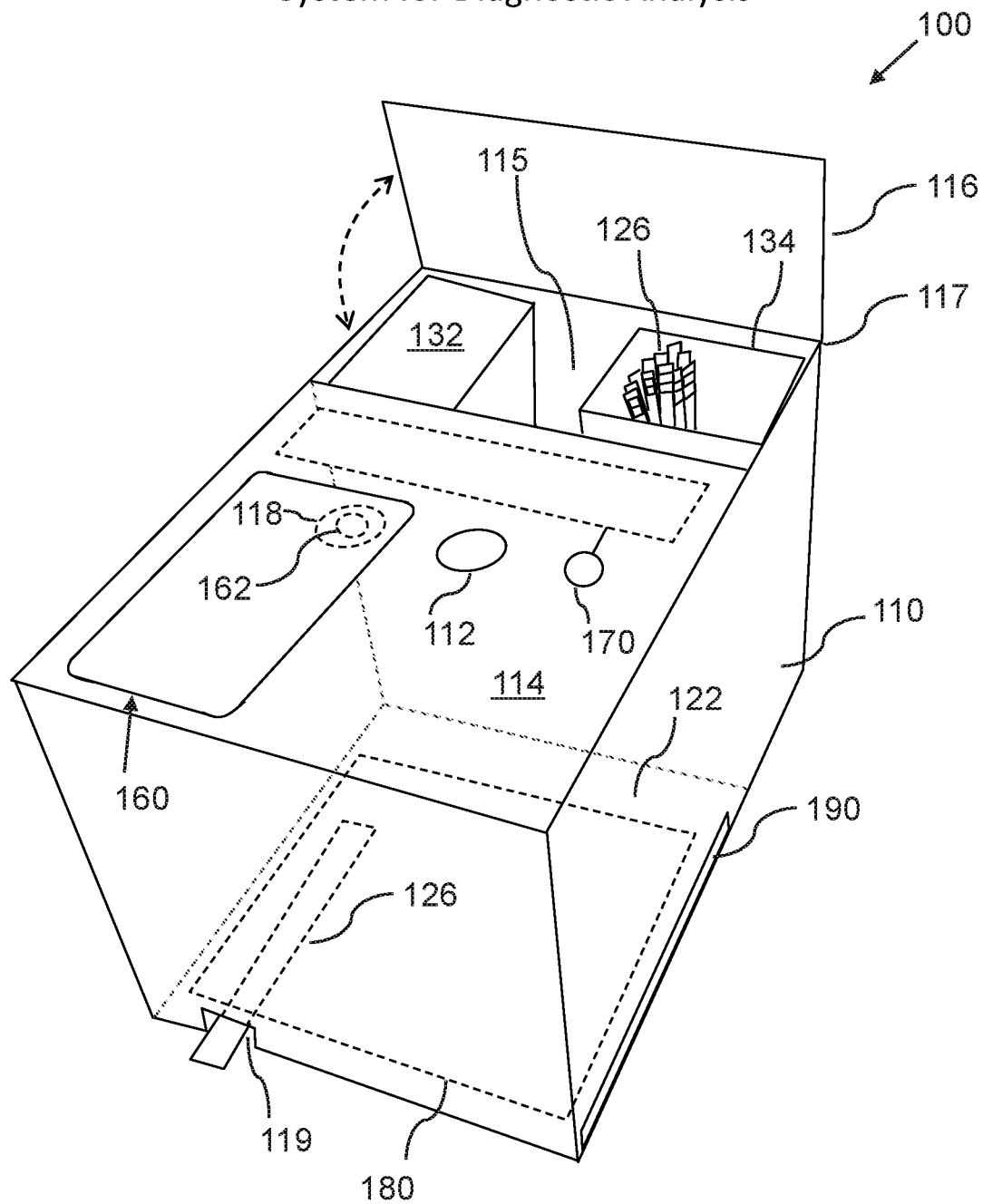
FIG. 1B is a perspective view of a system for diagnostic analysis, according to an embodiment of the invention.

In an embodiment, as shown in FIGS. 1A and 1B, a system for diagnostic analysis 100 can include:
a) a testing box 110, which can also be referred to as a diagnostic analysis tester 110, comprising sides defining an enclosure, such that the testing box 110 can further include:
  i. a testing chamber 114, which is a cavity inside the testing box 110;
  ii. a utility storage cavity 115, which is configured to store items for use in the system for diagnostic analysis 100, such as batteries with power switch 132, reagent strip container 134 including test strips 126 stored inside the reagent strip container 134, liquid dropper, cleaning tool, cable connectors to various type of smartphones and mobile devices, etc., such that a plurality of test strips 126 can be contained within the utility storage cavity 115;
  iii. a storage lid 116, which can be pivotally attached 117 to a side of the utility storage cavity, such that the storage lid 116 can be opened to provide access to the utility storage cavity 115;
  iv. a camera aperture 118, which is an aperture that provides visual access to the testing chamber 114;
  v. a visual check aperture 112, which is an aperture that provides visual access to the testing chamber 114, such that the visual check aperture 112 allows human monitoring and verification. The dual mode apertures 118, 112 allows swift human check of the key test parameters and proper setup via the visual check aperture 112, while the diagnostic analysis device 160 performs diagnostic analysis via the camera aperture 118;
  vi. a test slot 119, which is an aperture in the testing box 110, configured to insert a test strip 126 into the testing chamber 114; and
b) a diagnostic analysis device 160, which includes a camera lens 162, such that the diagnostic analysis device 160 for example as shown can be a smart phone 160, such that the diagnostic analysis device 160 can be positioned on the testing box 110 with the camera 162 adjacent to the camera aperture 118, as shown in FIG. 1B, such that the diagnostic analysis device 160 can capture an image of the inside of the testing chamber 114 the image comprising a diagnostic image part of a diagnostic portion 227 of the test strip 126, when as shown the test strip 126 is inserted through the test slot 119 with the diagnostic portion 227 of the test strip 126 inside the testing chamber 114;
wherein the analysis device is configured to analyze the diagnostic portion of the image, in order to calculate at least one test result or a plurality of test results.

Figure 2:
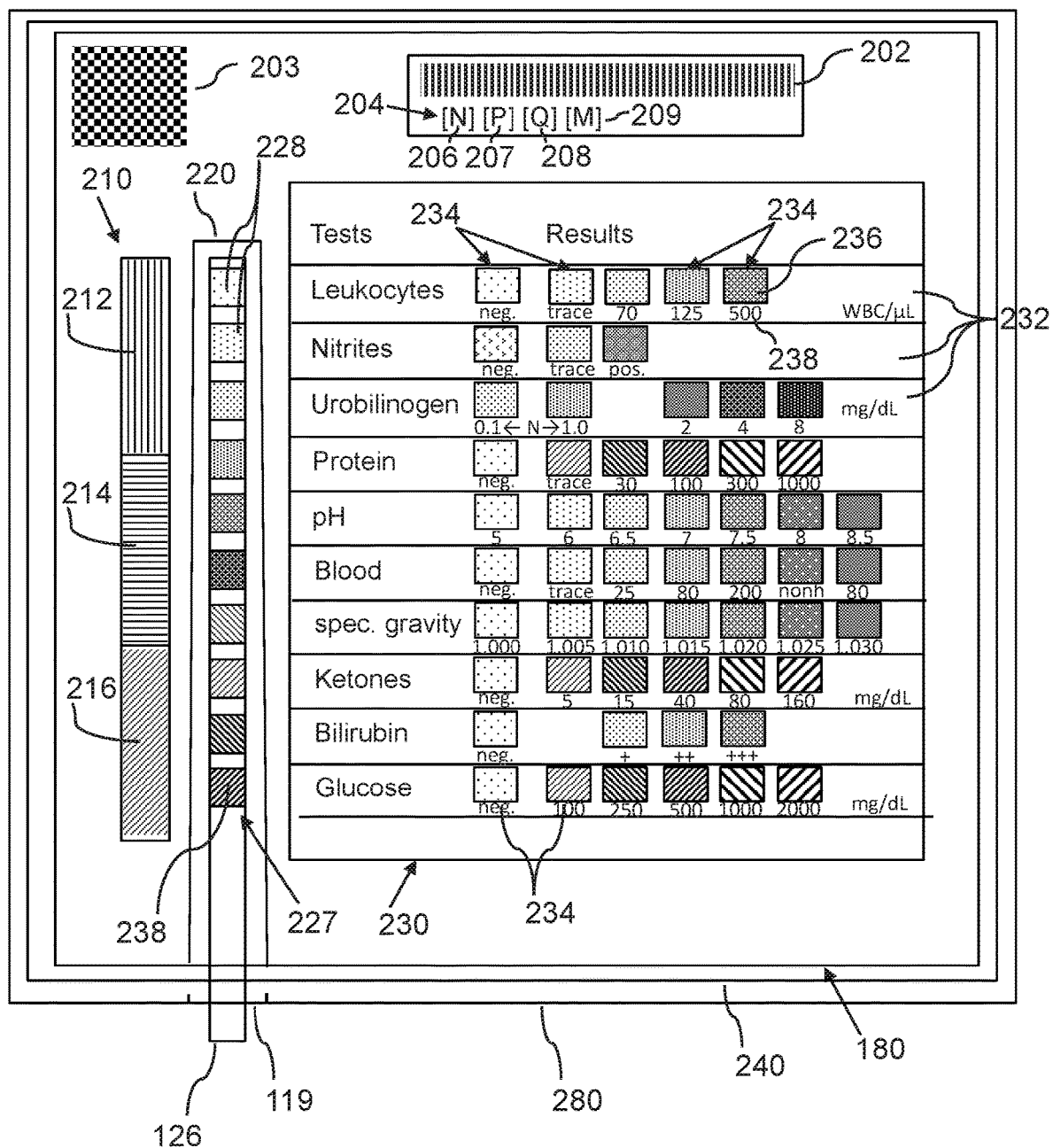
FIG. 2 is a top view of a bottom plate inside of the system for diagnostic analysis, according to an embodiment of the invention.

In a related embodiment, FIG. 2 shows an inside testing surface 280 of the testing chamber 114, typically positioned on an inside bottom 122 of the testing chamber 114, such that the inside testing surface is configured to receive and/or display:
a) an interchangeable color pattern chart 180, as also shown in outline in FIGS. 1A and 1B, the interchangeable color pattern chart 180 including:
  i. a chart bar code 202, which can be positioned on a top part of the interchangeable color pattern chart, such that the chart bar code 202 is configured to identify the interchangeable color pattern chart 180, which is associated with a specific test strip 126, with a predetermined type, make, and model of the test strip 126, including a specific manufacturer, and its product specifications, product batch number, etc., such that the chart bar code 202 indicates the corresponding interchangeable color pattern chart 180 that is currently inserted into or displayed in the testing chamber 114, whereby the chart bar code 202 indicates the corresponding interchangeable color pattern chart 180 to be used, such the chart bar code 202 can be used to direct the diagnostic analysis device 160 processing, while the visual/textual aspects of the corresponding interchangeable color pattern chart 180 can be interpreted by human eye reading, thereby providing a dual-mode design and operation. The interchangeable color pattern chart 180 chart bar code 202 can include a readable/textual test description 204, which can include a test product manufacturer 206, a test product name 207, a test product specification 208 (which for example can be a test capacity), and a test product batch number 209, wherein the readable test description 204 can be positioned adjacent to (such as below) the chart bar code 202;

ii. a product bar code 203, which can be a QR code 203, wherein the product bar code 203 can be configured to enable download of software (i.e. for example an app) for the diagnostic analysis device 160, along with product user instructions for use of the system for diagnostic analysis 100 and the diagnostic analysis device 160;

iii. a test result area 220, which is configured to receive a diagnostic portion 227 of the test strip 126 that is inserted into the testing chamber 114 through the test slot 119, wherein the diagnostic portion 227 of the test strip 126, comprises at least one test result pad 238 or a plurality of test result pads 238; and iv. a test lookup area 230, which includes a plurality of test lookup lines 232, each used for lookup/measurement of a diagnostic test result shown by a corresponding test result pad 228, each test lookup line 232, including a plurality of test lookup measures 234, each test lookup measure 234 including a test measure color 236 and a symbolic test measure 234, that can be a character string, a number, or a combination of these, such that the symbolic test measure 234 is associated with the color sample. The test lookup measures 234 can for example be ordered by symbolic test results, from negative, through trace, or normal results, to increasing degrees of positive diagnostic results;

such that the test lookup area 230 can be used for human analysis or validation of a test result from a test strip 126; and can also be used by the image analyzer 814 to load a test lookup matrix 430 for use in calculating a test result;

wherein the interchangeable color pattern chart 180 can be positioned on an inside bottom 122 of the testing chamber 114.

In a related embodiment, the testing box 110 can further include:

a) a graphic display panel 240, which can be positioned on an inside bottom 122 of the testing chamber 114;

such that the graphic display panel 240 is configured to display the interchangeable color pattern chart 180, whereby a first interchangeable color pattern chart 180 can be replaced with a second interchangeable color pattern chart 180 by changing an image shown on the graphic display panel 240; such that the graphic display panel 240 presents a predetermined test lookup area 230, which corresponds to the chart bar code 202, such that the test lookup area 230 corresponds to the product specifications indicated in the chart bar code 202, such that the predetermined test lookup area 230 is pre-saved and retrieved from the memory 804.

In a further related embodiment, the graphic display panel 240 can for example can be a 7-inch TFT high resolution LCD display panel.

In another further related embodiment, the graphic display panel 240 including the test lookup area 230 can be automatically turned on when a cable or Bluetooth connection is made with the diagnostic analysis device 160.

Figure 5:
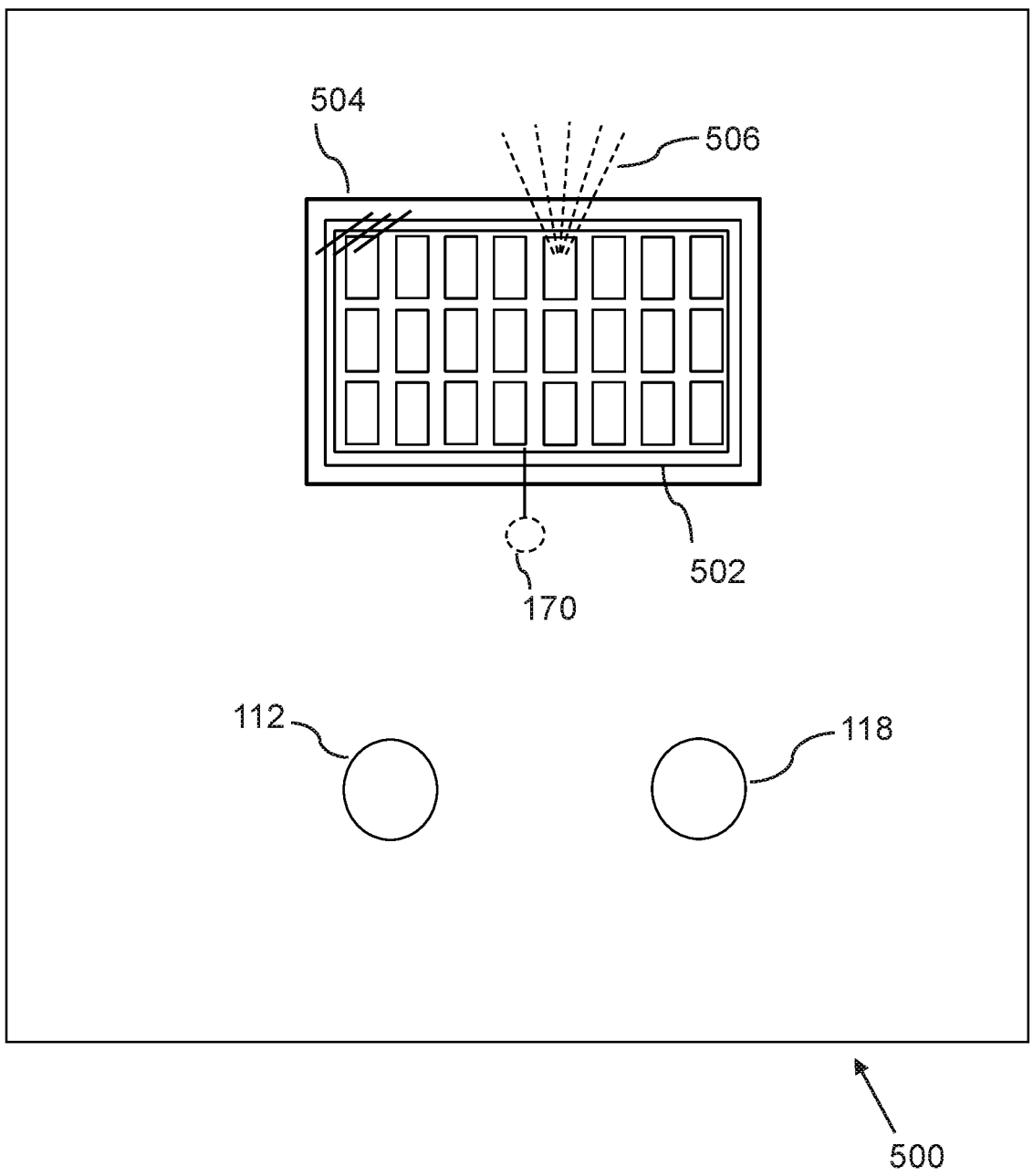
FIG. 5 is a bottom view of a top plate inside of the system for diagnostic analysis, according to an embodiment of the invention.

In a related embodiment, FIG. 5 shows an inside top surface 500 of the testing chamber 114, positioned on an inside top of the testing box 110, the inside top surface 500 including:

a) A light-emitting diode assembly 502, which is configured to illuminate the interchangeable color pattern chart 180, when the interchangeable color pattern chart 180 is inserted onto a bottom inner surface 280 of the testing chamber 114;

b) A color temperature correction filter 504, which can be positioned on a top of the light-emitting diode assembly 502, wherein the color temperature correction filter 504 is configured to adjust a color temperature of light 506 emitted from the light-emitting diode assembly 502 to a range of 5550 to 5650 Kelvin, or another preferred range, to enable the diagnostic analysis device 160 to perform more accurate color distance calculations, and thereby deliver accurate testing results;

c) The camera aperture 118; and d) The visual check aperture 112.

In a related embodiment, as shown in FIG. 6, the system for diagnostic analysis system 100 can include:

a) A diagnostic analysis server 602, which can store test lookup matrices 430 and test results, and perform analytics and reporting functions;

b) A diagnostic analysis box 110; and c) A diagnostic analysis device 160; which is connected to the diagnostic analysis server 602, in order to:

i. Scan a chart bar code 202 of an interchangeable color pattern chart 180 that is inserted into a testing chamber 114 of the diagnostic analysis box 110, to determine a bar code value 433;

ii. Retrieve a test lookup matrix 430 from test matrix database 710 of the diagnostic analysis server 602, wherein the test lookup matrix 430 is associated with the bar code value 433;

iii. Create, process, and store test lookup matrices 430, iv. Capture an original image 300 of an inside of the diagnostic analysis box 110 with a test strip 126 and an interchangeable color pattern chart 180 included therein;

v. Process the original image 300 to calculate a test result;

vi. Store the test results in the test result database 712 of the diagnostic analysis server 602.

In a related embodiment, as shown in FIG. 7, a diagnostic analysis server 602 can include:

a) A processor 702;

b) A non-transitory memory 704;

c) An input/output component 706;

d) A test matrix database 710, which can be configured to store and process at least one or a plurality of test lookup matrices 430;

e) A test result database 712; all connected via f) A data bus 720.

In a related embodiment, as shown in FIG. 8, a diagnostic analysis device 160 can include:

a) A processor 802;

b) A non-transitory memory 804;

c) An input/output 806;

d) A diagnostic manager 810, which is configured to process, store, and present diagnostic test results;

e) A camera manager 812;

f) An image analyzer 814;

g) A camera calibrator 815; and h) A camera 816, all connected via i) A data bus 820.

In a related embodiment, the testing box 110 can be configured as a 6 inch×6 inch×6 inch box.

In a related embodiment, the camera aperture 118 can be configured with a one-inch diameter.

In a related embodiment, the light-emitting diode assembly 502 can be configured to emit pure white light in a range of 4000-7000 Kelvin, such as for example about 5000 Kelvin.

In a related embodiment, the light-emitting diode assembly 502 can be configured as a 3×8 LED matrix panel.

In a related embodiment, a test strip 126 can include at least one or a plurality of test result pads 228, also referred to as chemical pads 228.

In a related embodiment, the test strip 126 can include a urine reagent test strip, which can include at least one or a plurality of test result pads 228, such as 1-14 pads 228, which are configured to test respectively 1 to 14 parameters. The chemical pads can for example be configured to test, individually or jointly, at least one or a combination of: Ketone, pH, Leukocytes, Urobilinogen, Microalbumin, Protein, Bilirubin, Glucose, Ascorbic Acid, Specific Gravity, Nitrite, Creatinine, Blood, and Calcium, in urine deposited on the chemical pads. There are many companies manufacturing reagent strips 126 for urine tests, saliva test, etc. As a result, product specifications are different, i.e. color patterns and required reaction time vary from product to product.

In a further related embodiment, the test strip 126 can be a urine reagent test strip, comprising at least one chemical test pad 228, which is selected from the group consisting of:

a) a ketone test pad;
b) a pH test pad;
c) a leukocytes test pad;
d) a urobilinogen test pad;
e) a microalbumin test pad;
f) a protein test pad;
g) a bilirubin test pad;
h) a glucose test pad;
i) an ascorbic acid test pad;
j) a specific gravity test pad;
k) a nitrite test pad;
l) a creatinine test pad;
m) a blood test pad;
n) a calcium test pad; and
o) combinations thereof.

In a related embodiment, the testing box 110 can further include a side slot 190, positioned in a side of the testing box 110, near the bottom of the testing box 110, as shown in FIG. 1A and FIG. 1B, such that the side slot 190 is configured to allow inserting an interchangeable color pattern chart 180 into the testing chamber 114, whereby a first interchangeable color pattern chart 180 can be replaced with a second interchangeable color pattern chart 180. Such interchangeable color pattern charts 180 can for example be made as printed cardboard or paper, which can be laminated.

In a related embodiment, the testing box 110 can further include a touch switch 170 that is connected to the light-emitting diode assembly 502, which can be configured to be triggered by a fingertip to turn the light-emitting diode assembly 502 on.

Figure 3:
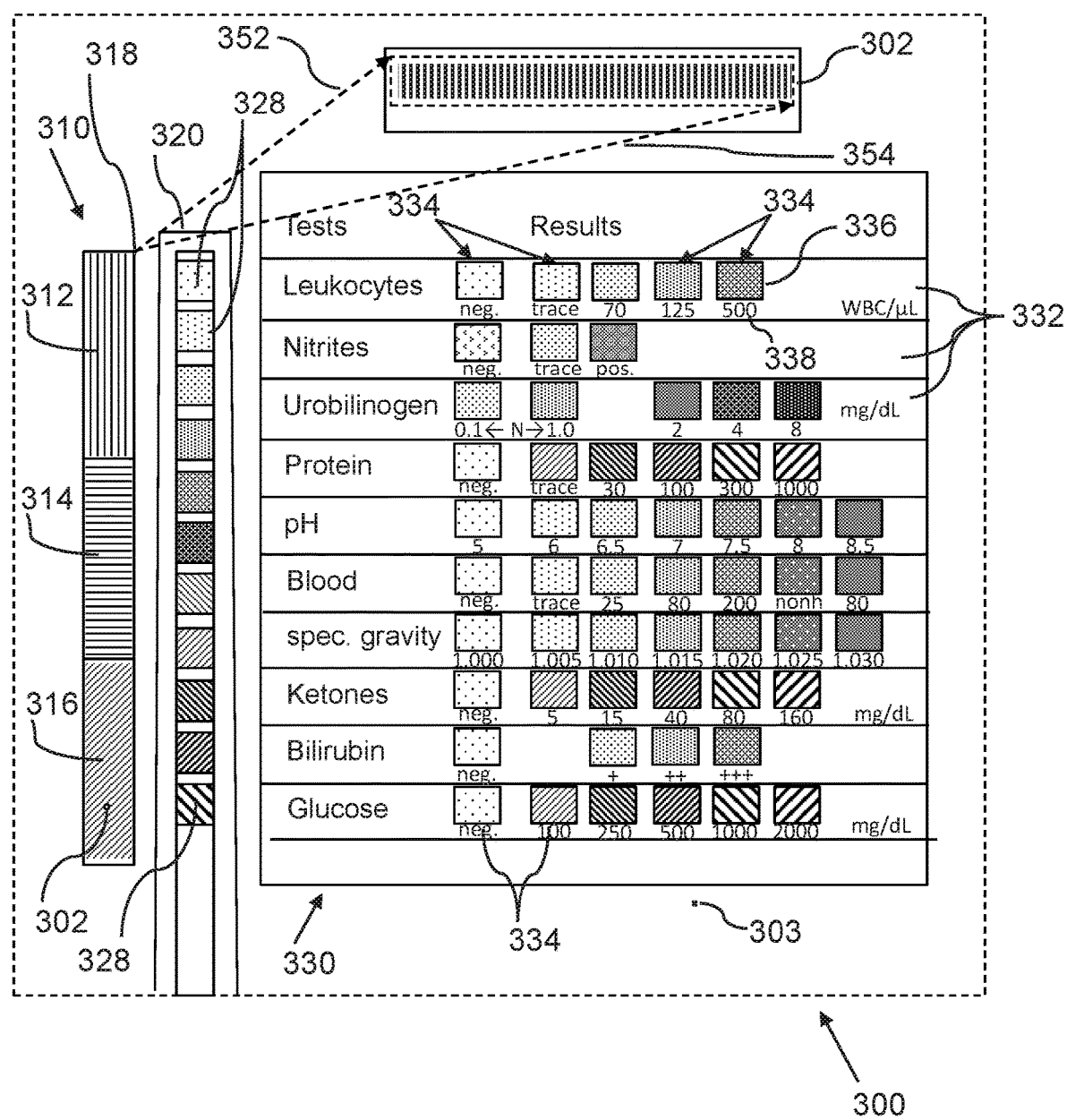
FIG. 3 is a view of an image of the bottom plate inside of the system for diagnostic analysis, taken by a camera of a diagnostic analysis device, according to an embodiment of the invention.

In a related embodiment, the camera manager 812 can be configured to control the camera 816 and capture an original image 300 of the interchangeable color pattern chart 180, as shown in FIG. 3. In a further related embodiment, the image analyzer 814, can be configured to extract image parts 302 310 312 314 316 320 328 330 332 334 336 338 of the original image 300, including:

a) a bar code image part 302, corresponding to the chart bar code 202;
b) a base color calibration strip image part 310, corresponding to the red-green-blue base color calibration strip 210, the base color calibration strip image part including a red color image part 312, a green color image part 314, and a blue color image part 316, corresponding respectively to the red calibration area 212, the green calibration area 214, and the blue calibration area 216;
c) a test strip image part 320, corresponding to the test result area 220 with a test strip 126 inserted through the test slot 119 and onto the test result area 220, the test strip image part 320 including at least one test result image part 328, corresponding to the at least one test result pad 228; and
d) a test lookup area image part 330, which is an image part of (i.e. corresponding to) the test lookup area 230, wherein the test measurement area image part 330 includes: a plurality of test measurement line image parts 332, each including a plurality of test measure image parts 334, each including a test measure color image part 336 and a symbolic test measure image part 338.

In a further related embodiment, the image analyzer 814 can extract (i.e. crop) the image parts 302 310 312 314 316 320 328 330 332 334 336 338 by first matching a location of the base color calibration strip image part 310, using well-known methods of image recognition and matching of reference images with a test image, and then normalizing the size of the original image 300 relative to the base color calibration strip image part 310, to create a normalized image, and extracting the bar code, test strip, and test lookup/measurement area image parts 302 320 330, by a relative location reference calculated from a base color calibration strip area position 318 in the normalized image using predetermined offset position vector pairs 352 354, as shown in FIG. 3, which are defined for each image part, wherein the offset position vector pairs 352 354 are specific to the interchangeable color pattern chart 180.

In a further related embodiment, the image analyzer 814 can be configured to process the original image 300 in order to load a test lookup matrix 430, as a structured internal representation, i.e. a data structure, of the test lookup area image part 330 (also called the test measurement area image part 330) of the original image 300.

Figure 4:
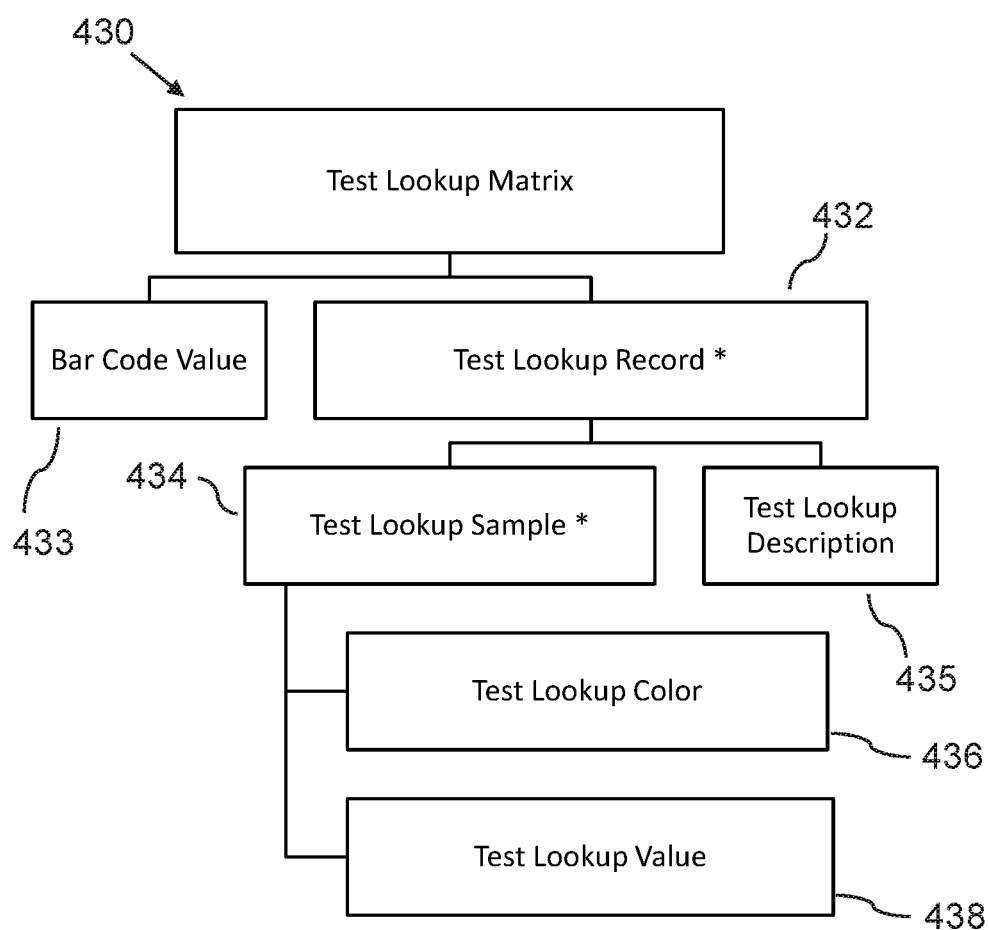
FIG. 4 is a schematic diagram illustrating a test lookup matrix, according to an embodiment of the invention.

In a yet further related embodiment, as shown in FIG. 4, a test lookup matrix 430 can include:

a) a bar code value 433, which identifies the interchangeable color pattern chart 180, and associated type (make and model) of test strip 126,
b) a plurality of test lookup records 432, for example implemented as a set or list, in the form of an array or linked list, each test lookup record 432 including:
  i. a plurality of test lookup samples 434, each including:
    a test lookup color 436, which can be predetermined or can be calculated by the image analyzer 814 via processing of an image 330, by averaging samples of color values within a corresponding test measure color image part 336; and
    a test lookup value 438, which can be predetermined or can be calculated by via optical character recognition of a symbolic test measure image part 338 associated with the test measure color image part 336, via well-known methods/algorithms of optical character recognition;

ii. a test lookup description 435, which describes the particular test associated with the test lookup record 432, such as for example "Ketone test".

In a related embodiment, the image analyzer 814 of the diagnostic analysis device 160 can be configured to set a timer to capture the first image 30 seconds after a test strip has been inserted into the testing chamber 114, and then start image processing. In a further related embodiment, (depending type of products indicated in the bar code) the image analyzer 814 can be further configured to capture subsequent second and third images after 60 and 120 seconds respectively. In a further related embodiment, the image analyzer 814 can be configured to detect insertion of the test strip 126, by using well-known methods/algorithms of motion detection, i.e. by using a motion detection algorithm, to detect a motion in the test result area 220.

In a related embodiment, the image analyzer 814 of the diagnostic analysis device 160 can be configured to set a timer to capture the first image at a first predetermined time after a test strip has been inserted into the testing chamber 114, and then start image processing, wherein the first predetermined time can be in a range of 15-45 seconds after the test strip has been inserted into the testing chamber.

In a further related embodiment, depending on the type of products indicated in the bar code, the image analyzer 814 can be further configured to capture subsequent second and third images at second and third predetermined times, respectively;
wherein the second predetermined time can be in a range of 45-75 seconds after the test strip has been inserted into the testing chamber; and wherein the third predetermined time can be in a range of 75-200 seconds after the test strip has been inserted into the testing chamber.

In a related embodiment, the camera calibrator 815 of the diagnostic analysis device 160 can be configured to determines a color calibration vector by analysis of an RGB base color bar image part of the image 300, which shows an RGB base color bar of the interchangeable color pattern chart, such that the color calibration vector includes a red calibration adjustment, a green calibration adjustment, and a blue calibration adjustment, such that the color calibration vector is applied to average measured red, green, and blue values from the red color image part 312, the green color image part 314, and the blue color image part 316, respectively, in order to calculate predetermined red, green, or blue standard calibration values. A calibration adjustment can be determined as an additive offset from a predetermined red, green, or blue baseline value, that is added in order to get the measured values (which can be an average over the extracted area), or it can be determined as an offset factor from a predetermined red, green, or blue standard value, that is multiplied in order to get the measured value.

In a related embodiment, the image analyzer 814 of the diagnostic analysis device 160 can be configured to apply the color calibration vector as an offset calculation on the original image 300, which can be an additive or multiplicative offset calculation such that each original pixel of the original image is corrected, such that the calibration vector is applied (as an additive or multiplicative offset) to red, green, and blue pixel values of each original pixel 303; such that the color calibration vector is applied to average measured red, green, and blue values from the red color image part, the green color image part, and the blue color image part, respectively, in order to calculate predetermined red, green, or blue baseline calibration values; wherein the image analyzer is configured to apply the color calibration vector as an offset calculation on the original image 300, such that the color calibration vector is applied to red, green, and blue pixel values of each original pixel 303 of the original image 300. Similar methods can be applied to images 300 encoded in some other color space, such as hue-saturation-value, hue-saturation-luminance, CIE XYZ, etc.

In a related embodiment, the image analyzer 814 of the diagnostic analysis device 160 can be configured to apply the color calibration vector as an offset calculation on the original image, which can be an additive offset calculation such that each original pixel of the original image is corrected, such that the calibration vector is added to red, green, and blue pixel values of each original pixel.

In a related embodiment, the image analyzer 814 of the diagnostic analysis device 160 can be configured to apply the color calibration vector as an offset calculation on the original image, which can be a multiplicative offset calculation such that each original pixel of the original image is corrected, such that the calibration vector is multiplied with red, green, and blue pixel values of each original pixel.

In a related embodiment, the image analyzer 814 can be configured to convert RGB values of the image parts 302 310 312 314 316 320 328 330 332 334 336 338 of the original image 300 to HSV color space, for color distance calculations.

In a further related embodiment, the image analyzer 814 can be configured to determine a decoded bar code value 433 by a decoding of the bar code image part 302, such that the image analyzer can determine a corresponding test lookup matrix 430 with a corresponding bar code value 433 that matches the decoded bar code value 433.

In a further related embodiment, the image analyzer 814 can be configured to calculate matching or nearest color values (i.e. with minimum color distance under a color coding metric) from a measured test result image part 328 to a matching test lookup color 436, thereby determining a test lookup value 438 that corresponds to the test lookup color 436, whereby the test lookup value 438 is the test result value, wherein the nearest color value is determined based on a color distance calculation, according to well-known methods of color distance calculation, such as for example Euclidian distance in an RGB or HSV color space, or LAB Delta E color distance calculations, defined by the INTERNATIONAL COMMISSION ON ILLUMINATION™, including CIE76™, CIE94™, or CIEDE2000™.

In a related embodiment, the diagnostic manager 810 can be configured to format and present calculated test results for review by a user 622.

In a further related embodiment, the diagnostic manager 810 can communicate with the diagnostic analysis server, to store test results, for example in cloud storage, and utilize advanced data management, reporting, and analytics features. Summary reports can be sent back to the diagnostic analysis device 160, along with trending indication highlights.

In another embodiment, the test matrix database 710 of the diagnostic analysis server 602, can be configured to store at least one or a plurality of test lookup matrices 430, each associated with a chart bar code 202 value. The diagnostic manager 810 of the diagnostic analysis device can be configured to retrieve a test lookup matrix 430 in communication with the test matrix database 710 of the diagnostic analysis server 602, such that the test lookup matrix 430 is associated with a particular chart bar code 202.

In a related embodiment, the system for diagnostic analysis 100 can include a control unit, including 64 GB flash memory storage, 3-in-one mobile device connectors, Bluetooth™ Transmitter/Receiver module and a 4-inch TFT LCD touch screen display to utility storage cavity 115. The control unit with 64 GB flash memory can be connected with the battery unit, it can also be connected to a 4-inch LCD touch screen display (3.8×2.3) which is attached to the lid (inside), and a 7-inch high resolution LCD display in the testing chamber. When the lid 116 is opened, the display is turned on automatically. Welcome screen with icons of up to 4 users are shown. When selecting a user, pre-stored information of up to 10 recent test results in a bar chart come up to the screen, along with the average trending line indicators. The control unit connects one end of USB cable (USB-A) and 3-in-one mobile connectors (Lightning port, Micro USB, and USB-C) are offered on the other end, enabling connections with different mobile devices 160. Alternatively, a wireless connection, such as BLUETOOTH™ can be used instead of a connector cable.

In related embodiments, the diagnostic analysis device 160 can include configurations as:
- a) A web application, executing in a Web browser;
- b) A mobile app, executing on a mobile device, such for example an Android phone or iPhone, any smartphone device, or wearable mobile device;
- c) A tablet app, executing on a tablet device, such as for example an Android or iOS tablet device;
- d) A desktop application, executing on a personal computer with a connected external camera, or similar device; or
- e) Any computer device with Internet connectivity.

It shall be understood that an executing instance of an embodiment of the system for diagnostic analysis 100, as shown in FIGS. 1A, 1B and 6, can include a plurality of diagnostic analysis devices 160, which are each tied to one or more users 622.

An executing instance of an embodiment of the system for diagnostic analysis 100, as shown in FIG. 6, can similarly include a plurality of diagnostic analysis servers 602.

In an embodiment, as illustrated in FIG. 9, a method for diagnostic analysis 900 can include:
- a) Installing an interchangeable color pattern chart 902, wherein the interchangeable color pattern chart 180 is installed in a testing chamber 114 of a diagnostic analysis tester 110;
- b) Depositing a diagnostic sample 904, which can for example be a urine sample, or a sample of another bodily fluid, wherein the diagnostic sample is deposited on a reagent test strip 126, such that the reagent test strip 126 is compatible with the interchangeable color pattern chart 180;
- c) Inserting the reagent test strip 906, wherein the reagent test strip 126 is inserted into a test slot 119 of the diagnostic analysis tester onto the interchangeable color pattern chart 180 inside the testing chamber 114, such that a diagnostic portion 227 of the reagent test strip 126 is exposed to illumination from a light-emitting diode assembly 502 mounted inside the testing chamber 114;
- d) Capturing an original image 908, wherein the original image is captured with a diagnostic analysis device 160, which can be a smart phone 160, which is positioned on a top outside of the diagnostic analysis tester 110, such that a camera lens 162 of the diagnostic analysis device 160 is positioned on a top of a camera aperture 118 of the diagnostic analysis tester 110, such that the camera aperture 118 is configured to provide visual access to the testing chamber 114 for inspection and verification by a user 622;
- e) Performing color calibration 910, wherein an image analyzer 814 of the diagnostic analysis device 160 determines a color calibration vector by analysis of an RGB base color bar image part of the image, which shows an RGB base color bar of the interchangeable color pattern chart;
- f) Reading a bar code 912, when the image analyzer 814 reads the bar code from the interchangeable color pattern chart, such that if the bar code is unknown the process restarts from Installing an interchangeable color pattern chart 902,
    wherein the image analyzer determines a bar code value by a decoding of a bar code image part and identifying a test lookup matrix that matches the bar code value;
    wherein the test look up matrix comprises:
        a plurality of test lookup records, each comprising:
            a plurality of test lookup samples, each comprising:
                a test lookup color; and
                a test lookup value;
- g) Extracting test strip image 914, wherein a crop of the test strip is extracted from the image, a list of color squares is extracted, and a color noise reduction process is executed for each color square in the list of color squares;
- h) Performing color conversion 916, wherein an RGB representation of the list of color squares is converted to an HSV representation; and
- i) Calculating a test result 918, wherein the test result is calculated, by finding a zero or minimal color distance from a measured test result image part 328 to a matching test lookup color 436 in a test lookup matrix 430, thereby determining a test lookup value 438 that corresponds to the test lookup color 436, whereby the test lookup value 438 is the test result.

FIGS. 1A, 1B, 6, 7, 8 and 9 are block diagrams and flowcharts, methods, devices, systems, apparatuses, and computer program products according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIGS. 1A, 1B, 6, 7, and 8 depict the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include various forms of non-transitory storage media such as random access memory (RAM) and read-only memory (ROM). The computer also may include nonvolatile storage memory, such as a hard disk drive, where additional data can be stored.

FIG. 6 shows a depiction of an embodiment of the system for diagnostic analysis 100, including the diagnostic analysis server 602, and the diagnostic analysis device 160. In this relation, a server shall be understood to represent a general computing capability that can be physically manifested as one, two, or a plurality of individual physical computing devices, located at one or several physical locations. A server can for example be manifested as a shared computational use of one single desktop computer, a dedicated server, a cluster of rack-mounted physical servers, a datacenter, or network of datacenters, each such datacenter containing a plurality of physical servers, or a computing cloud, such as Google Cloud, Amazon EC2 or Microsoft Azure.

It shall be understood that the above-mentioned components of the diagnostic analysis server 602 and the diagnostic analysis device 160 are to be interpreted in the most general manner.

For example, the processors 702 802, can each respectively include a single physical microprocessor or microcontroller, a cluster of processors, a datacenter or a cluster of datacenters, a computing cloud service, and the like.

In a further example, the non-transitory memory 704 and the non-transitory memory 804 can each respectively include various forms of non-transitory storage media, including random access memory and other forms of dynamic storage, and hard disks, hard disk clusters, cloud storage services, and other forms of long-term storage. Similarly, the input/output 706 and the input/output 806 can each respectively include a plurality of well-known input/output devices, such as screens, keyboards, pointing devices, motion trackers, communication ports, and so forth.

Furthermore, it shall be understood that the diagnostic analysis server 602 and the diagnostic analysis device 160 can each respectively include a number of other components that are well known in the art of general computer devices, and therefore shall not be further described herein. This can include system access to common functions and hardware, such as for example via operating system layers such as Windows, Linux, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

In a related embodiment, the diagnostic analysis device 160 communicates with the diagnostic analysis server 602 over a network 606, which can include the general Internet, a Wide Area Network or a Local Area Network, or another form of communication network, transmitted on wired or wireless connections. Wireless networks can for example include Ethernet, Wi-Fi, Bluetooth, ZigBee, and NFC. The communication can be transferred via a secure, encrypted communication protocol.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Here has thus been described a multitude of embodiments of the system for diagnostic analysis 100, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

For example, alternative embodiments can reconfigure or combine the components of the diagnostic analysis server 602 and the diagnostic analysis device 160. The components of the diagnostic analysis server 602 can be distributed over a plurality of physical, logical, or virtual servers. Parts or all of the components of the diagnostic analysis device 160 can be configured to operate in the diagnostic analysis server 602, whereby the diagnostic analysis device 160 for example can function as a thin client, performing only graphical user interface presentation and input/output functions. Alternatively, parts or all of the components of the diagnostic analysis server 602 can be configured to operate in the diagnostic analysis device 160.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A system for diagnostic analysis, comprising:
a) a testing box, comprising sides defining an enclosure, the testing box further comprising:
  a testing chamber, which is configured as a cavity inside the testing box;
  a camera aperture, which is a first aperture in the testing box, such that the camera aperture is configured to provide visual access to the testing chamber; and
  a test slot, which is a second aperture in the testing box, configured to allow insertion of a test strip into the testing chamber; and
b) a diagnostic analysis device, which comprises a camera, such that the diagnostic analysis device is configured to be positioned on the testing box with the camera adjacent to the camera aperture, such that when the test strip is inserted into the test slot, the diagnostic analysis device is configured to capture an original image of an inside of the testing chamber, the original image comprising a test strip image part corresponding to a diagnostic portion of the test strip, the test strip image part comprising at least one test result image part; and
c) an interchangeable color pattern chart, comprising:
  a chart bar code, such that the chart bar code is configured to identify the interchangeable color pattern chart;
  a base color calibration strip, comprising a red calibration area, a green calibration area, and a blue calibration area;
  a test result area, which is configured to receive the diagnostic portion of the test strip when the test strip is inserted through the test slot into the testing chamber; and
  a test lookup area, which includes a plurality of test lookup lines, each test lookup line including a plurality of test lookup measures, each test lookup measure including a test measure color and a symbolic test measure that is associated with the test measure color;
  wherein the interchangeable color pattern chart is positioned on an inside bottom of the testing chamber;
wherein the diagnostic analysis device is configured to analyze the at least one test result image part of the original image and calculate at least one test result value;
wherein the testing box further comprises:
  a light-emitting diode assembly, which is configured to illuminate the interchangeable color pattern chart; and
  a color temperature correction filter, which is positioned on a top of the light-emitting diode assembly;
  wherein the light-emitting diode assembly is positioned on an inside top surface of the testing chamber; and
  wherein the color temperature correction filter is configured to adjust a color temperature of light emitted from the light-emitting diode assembly, whereby the color temperature correction filter is configured to enable the diagnostic analysis device to perform accurate color distance calculations, and thereby deliver accurate testing results.

2. The system for diagnostic analysis of claim 1, wherein the testing box further comprises:
a) a utility storage cavity, which is configured to store items for use in the system for diagnostic analysis; and
b) a storage lid, which is pivotally attached to a side of the utility storage cavity, such that the storage lid is configured to provide access to the utility storage cavity.

3. The system for diagnostic analysis of claim 2, further comprising a plurality of test strips that are contained within the utility storage cavity.

4. The system for diagnostic analysis of claim 1, wherein the diagnostic analysis device is a smart phone.

5. The system for diagnostic analysis of claim 1, wherein the color temperature correction filter is configured to adjust the color temperature of the light emitted from the light-emitting diode assembly to a range of 5550 to 5650 Kelvin.

6. The system for diagnostic analysis of claim 1, wherein the diagnostic analysis device further comprises:
a) a processor;
b) a non-transitory memory;
c) an input/output component; and
d) a camera manager, which is configured to control the camera to capture the original image of the interchangeable color pattern chart, when the test strip is inserted through the test slot into the testing chamber and the test result area has received the diagnostic portion of the test strip; all connected via
e) a data bus.

7. The system for diagnostic analysis of claim 6, wherein the diagnostic analysis device further comprises:
an image analyzer, which is connected to the data bus;
wherein the image analyzer is configured to extract image parts of the original image, the image parts including:
a) a bar code image part, corresponding to the chart bar code of the interchangeable color pattern chart;
b) a base color calibration strip image part, corresponding to the base color calibration strip of the interchangeable color pattern chart, the base color calibration strip image part comprising a red color image part, a green color image part, and a blue color image part, corresponding respectively to the red calibration area, the green calibration area, and the blue calibration area;
c) the test strip image part, corresponding to the test result area, wherein the test strip image part comprises at least one test result image part, corresponding to at least one test result pad of the diagnostic portion of the test strip; and
d) a test measurement area image part, corresponding to the test lookup area, wherein the test measurement area image part comprises:
  a plurality of test measurement line image parts, each comprising a plurality of test measure image parts, each comprising a test measure color image part and a symbolic test measure image part.

8. The system for diagnostic analysis of claim 7, wherein the image analyzer is configured to extract the image parts by matching a location of the base color calibration strip image part, normalizing a size of the original image relative to the base color calibration strip image part to create a normalized image, and extracting the bar code image part, the test strip image part, and the test measurement area image part, by a relative location reference calculated from a base color calibration strip area position in the normalized image, using predetermined offset position vector pairs, which are defined for each image part, wherein the predetermined offset position vector pairs are specific to the interchangeable color pattern chart.

9. The system for diagnostic analysis of claim 7, wherein the image analyzer is configured to set a timer to capture a first image at a first predetermined time, wherein the first predetermined time is in a range of 15-45 seconds after the test strip has been inserted into the testing chamber;
wherein the image analyzer is configured to detect insertion of the test strip, by using a motion detection algorithm, to detect a motion in the test result area.

10. The system for diagnostic analysis of claim 9, wherein the image analyzer is further configured to capture a second image and a third image, at respectively second and third predetermined times;
wherein the second predetermined time is in a range of 45-75 seconds after the test strip has been inserted into the testing chamber;
wherein the third predetermined time is in a range of 75-200 seconds after the test strip has been inserted into the testing chamber.

11. The system for diagnostic analysis of claim 7, wherein the image analyzer is further configured to determine a bar code value by a decoding of the bar code image part and identify a test lookup matrix that matches the bar code value;
wherein the test lookup matrix comprises:
the bar code value;
a plurality of test lookup records, each comprising:
a plurality of test lookup samples, each comprising:
a test lookup color; and
a test lookup value.

12. The system for diagnostic analysis of claim 11, wherein the image analyzer is further configured to calculate a nearest color value from the at least one test result image part of the test strip image part to a matching test lookup color of the plurality of test lookup samples, thereby determining the test lookup value that corresponds to the matching test lookup color, whereby the test lookup value is the at least one test result value.

13. The system for diagnostic analysis of claim 7, wherein the diagnostic analysis device further comprises:
a camera calibrator, which is connected to the data bus;
wherein the camera calibrator is configured to calculate a color calibration vector by analysis of the base color calibration strip image part, such that the color calibration vector includes a red calibration adjustment, a green calibration adjustment, and a blue calibration adjustment;
such that the color calibration vector is applied to average measured red, green, and blue values from the red color image part, the green color image part, and the blue color image part, respectively, in order to calculate predetermined red, green, or blue baseline calibration values;
wherein the image analyzer is configured to apply the color calibration vector as an offset calculation on the original image, such that the color calibration vector is applied to red, green, and blue pixel values of each original pixel of the original image.

14. The system for diagnostic analysis of claim 1, further comprising the test strip, which is inserted through the test slot into the testing chamber.

15. The system for diagnostic analysis of claim 14, wherein the test strip is a urine reagent test strip, comprising at least one chemical test pad, which is selected from the group consisting of:
a) a ketone test pad;
b) a pH test pad;
c) a leukocytes test pad;
d) a urobilinogen test pad;
e) a microalbumin test pad;
f) a protein test pad;
g) a bilirubin test pad;
h) a glucose test pad;
i) an ascorbic acid test pad;
j) a specific gravity test pad;
k) a nitrite test pad;
l) a creatinine test pad;
m) a blood test pad;
n) calcium test pad; and
o) combinations thereof.

16. The system for diagnostic analysis of claim 1, wherein the testing box further comprises:
a side slot, which is positioned in a side of the testing box;
wherein the side slot is configured to allow insertion of the interchangeable color pattern chart into the testing chamber.

17. The system for diagnostic analysis of claim 1, wherein the testing box further comprises:
a visual check aperture, which is a third aperture in the testing box, such that the camera aperture is configured to provide visual access to the testing chamber for inspection and verification by a user.

18. The system for diagnostic analysis of claim 1, wherein the interchangeable color pattern chart further comprises:
a readable test description, which comprises a test product manufacturer, a test product name, and a test product batch number;
wherein the readable test description is positioned adjacent to the chart bar code.

19. The system for diagnostic analysis of claim 1, wherein the interchangeable color pattern chart further comprises:
a product bar code, which is configured to enable download of software for the diagnostic analysis device.

20. The system for diagnostic analysis of claim 1, wherein the testing box further comprises:
a graphic display panel, which is positioned on the inside bottom of the testing chamber;
such that the graphic display panel is configured to display the interchangeable color pattern chart;
wherein the graphic display panel shows a predetermined test lookup area, which corresponds to the chart bar code.

21. A method for diagnostic analysis using a system for diagnostic analysis, wherein the method comprises:
a) installing an interchangeable color pattern chart, wherein the interchangeable color pattern chart is installed in a testing chamber of a diagnostic analysis tester;
b) depositing a diagnostic sample, wherein the diagnostic sample is deposited on a test strip, such that the test strip is compatible with the interchangeable color pattern chart;
c) inserting the test strip, wherein the test strip is inserted into a test slot of the diagnostic analysis tester onto the interchangeable color pattern chart inside the testing chamber, such that a diagnostic portion of the test strip is exposed to illumination;
d) capturing an original image, wherein the original image is captured with a diagnostic analysis device, which is positioned on a top outside of the diagnostic analysis tester, such that a camera lens of the diagnostic analysis device is positioned on a top of a camera aperture of the diagnostic analysis tester, such that the camera aperture is configured to provide visual access to the testing chamber; and
e) calculating at least one test result value, wherein the at least one test result value is calculated by finding a minimal color distance from a measured test result image part to a matching test lookup color of a test lookup record in a test lookup matrix, thereby determining a test lookup value that corresponds to the matching test lookup color, whereby the test lookup value is the at least one test result value;
wherein the system for diagnostic analysis, comprises:
the diagnostic analysis tester, which comprises a testing box, comprising sides defining an enclosure, the testing box further comprising:
   the testing chamber, which is configured as a cavity inside the testing box;
   the camera aperture, which is a first aperture in the testing box, such that the camera aperture is configured to provide visual access to the testing chamber; and
   the test slot, which is a second aperture in the testing box, configured to allow insertion of a test strip into the testing chamber; and
the diagnostic analysis device, which comprises a camera, such that the diagnostic analysis device is configured to be positioned on the testing box with the camera adjacent to the camera aperture, such that when the test strip is inserted into the test slot, the diagnostic analysis device is configured to capture an original image of an inside of the testing chamber, the original image comprising a test strip image part corresponding to a diagnostic portion of the test strip, the test strip image part comprising at least one test result image part; and
the interchangeable color pattern chart, comprising:
   a chart bar code, which is configured to identify the interchangeable color pattern chart;
   a base color calibration strip, comprising a red calibration area, a green calibration area, and a blue calibration area; and
   a test result area, which is configured to receive the diagnostic portion of the test strip when the test strip is inserted through the test slot into the testing chamber; and
   a test lookup area, which includes a plurality of test lookup lines, each test lookup line including a plurality of test lookup measures, each test lookup measure including a test measure color and a symbolic test measure that is associated with the test measure color;
wherein the testing chamber is configured to receive the interchangeable color pattern chart;
wherein the diagnostic analysis device is configured to analyze the at least one test result image part of the original image and calculate at least one test result value
wherein the testing box further comprises:
   a light-emitting diode assembly, which is configured to illuminate the interchangeable color pattern chart; and
   a color temperature correction filter, which is positioned on a top of the light-emitting diode assembly;
   wherein the light-emitting diode assembly is positioned on an inside top surface of the testing chamber; and
   wherein the color temperature correction filter is configured to adjust a color temperature of light emitted from the light-emitting diode assembly, whereby the color temperature correction filter is configured to enable the diagnostic analysis device to perform accurate color distance calculations, and thereby deliver accurate testing results.

22. A system for diagnostic analysis, comprising:
a) a testing box, comprising sides defining an enclosure, the testing box further comprising:
   a testing chamber, which is configured as a cavity inside the testing box;
   a camera aperture, which is a first aperture in the testing box, such that the camera aperture is configured to provide visual access to the testing chamber; and
   a test slot, which is a second aperture in the testing box, configured to allow insertion of a test strip into the testing chamber; and
b) a diagnostic analysis device, which comprises a camera, such that the diagnostic analysis device is configured to be positioned on the testing box with the camera adjacent to the camera aperture, such that when the test strip is inserted into the test slot, the diagnostic analysis device is configured to capture an original image of an inside of the testing chamber, the original image comprising a test strip image part corresponding to a diagnostic portion of the test strip, the test strip image part comprising at least one test result image part; and
c) an interchangeable color pattern chart, comprising:
   a chart bar code, such that the chart bar code is configured to identify the interchangeable color pattern chart;
   a base color calibration strip, comprising a red calibration area, a green calibration area, and a blue calibration area;
   a test result area, which is configured to receive the diagnostic portion of the test strip when the test strip is inserted through the test slot into the testing chamber; and
   a test lookup area, which includes a plurality of test lookup lines, each test lookup line including a plurality of test lookup measures, each test lookup measure including a test measure color and a symbolic test measure that is associated with the test measure color;
wherein the interchangeable color pattern chart is positioned on an inside bottom of the testing chamber;
wherein the diagnostic analysis device is configured to analyze the at least one test result image part of the original image and calculate at least one test result value
wherein the testing box further comprises:
   a graphic display panel, which is positioned on the inside bottom of the testing chamber;
   such that the graphic display panel is configured to display the interchangeable color pattern chart;
   wherein the graphic display panel shows a predetermined test lookup area, which corresponds to the chart bar code.

23. A method for diagnostic analysis using a system for diagnostic analysis, wherein the method comprises:
a) installing an interchangeable color pattern chart, wherein the interchangeable color pattern chart is installed in a testing chamber of a diagnostic analysis tester;
b) depositing a diagnostic sample, wherein the diagnostic sample is deposited on a test strip, such that the test strip is compatible with the interchangeable color pattern chart;

c) inserting the test strip, wherein the test strip is inserted into a test slot of the diagnostic analysis tester onto the interchangeable color pattern chart inside the testing chamber, such that a diagnostic portion of the test strip is exposed to illumination;

d) capturing an original image, wherein the original image is captured with a diagnostic analysis device, which is positioned on a top outside of the diagnostic analysis tester, such that a camera lens of the diagnostic analysis device is positioned on a top of a camera aperture of the diagnostic analysis tester, such that the camera aperture is configured to provide visual access to the testing chamber; and e) calculating at least one test result value, wherein the at least one test result value is calculated by finding a minimal color distance from a measured test result image part to a matching test lookup color of a test lookup record in a test lookup matrix, thereby determining a test lookup value that corresponds to the matching test lookup color, whereby the test lookup value is the at least one test result value;

wherein the system for diagnostic analysis, comprises:
  the diagnostic analysis tester, which comprises a testing box, comprising sides defining an enclosure, the testing box further comprising:
    the testing chamber, which is configured as a cavity inside the testing box;
    the camera aperture, which is a first aperture in the testing box, such that the camera aperture is configured to provide visual access to the testing chamber; and
    the test slot, which is a second aperture in the testing box, configured to allow insertion of a test strip into the testing chamber; and
  the diagnostic analysis device, which comprises a camera, such that the diagnostic analysis device is configured to be positioned on the testing box with the camera adjacent to the camera aperture, such that when the test strip is inserted into the test slot, the diagnostic analysis device is configured to capture an original image of an inside of the testing chamber, the original image comprising a test strip image part corresponding to a diagnostic portion of the test strip, the test strip image part comprising at least one test result image part; and the interchangeable color pattern chart, comprising:
  a chart bar code, which is configured to identify the interchangeable color pattern chart;
  a base color calibration strip, comprising a red calibration area, a green calibration area, and a blue calibration area; and
  a test result area, which is configured to receive the diagnostic portion of the test strip when the test strip is inserted through the test slot into the testing chamber; and
  a test lookup area, which includes a plurality of test lookup lines, each test lookup line including a plurality of test lookup measures, each test lookup measure including a test measure color and a symbolic test measure that is associated with the test measure color;

wherein the testing chamber is configured to receive the interchangeable color pattern chart;

wherein the diagnostic analysis device is configured to analyze the at least one test result image part of the original image and calculate at least one test result value wherein the testing box further comprises:
  a graphic display panel, which is positioned on the inside bottom of the testing chamber;
  such that the graphic display panel is configured to display the interchangeable color pattern chart;
  wherein the graphic display panel shows a predetermined test lookup area, which corresponds to the chart bar code.

\* \* \* \* \*